United States Patent [19]
Carson

[11] Patent Number: 5,626,626
[45] Date of Patent: May 6, 1997

[54] IMPLANTABLE MEDICAL APPARATUS WITH MAGNIFYING HEADER

[75] Inventor: Dean F. Carson, Mountain View, Calif.

[73] Assignee: Ventritex, Inc., Sunnyvale, Calif.

[21] Appl. No.: 443,127

[22] Filed: May 17, 1995

[51] Int. Cl.$^6$ .................................................. A61N 1/36
[52] U.S. Cl. .................................................. 607/36
[58] Field of Search .................................. 607/36, 37, 38

[56] References Cited

U.S. PATENT DOCUMENTS 4,154,248  5/1979  Jones .
5,370,663  12/1994  Lin .............................................. 607/5

Primary Examiner—Marvin M. Lateef
Assistant Examiner—Scott M. Getzow
Attorney, Agent, or Firm—Steven M. Mitchell; Mark J. Meltzer; M. Elizabeth Bush

[57] ABSTRACT

An implantable medical apparatus operable in conjunction with an attachable lead, and having a housing containing an electronic component, with a header connected to the housing and defining a cavity. A connector element is positioned within the cavity and is operably connected to the electronic component. A lens is connected to the header, such that the connector element may be viewed through the lens to facilitate confirmation of proper connection of a lead to the connector. The header may be transparent, and the lens either formed as part of the header, or detachable therefrom.

14 Claims, 6 Drawing Sheets

IMPLANTABLE MEDICAL APPARATUS WITH MAGNIFYING HEADER

FIELD OF THE INVENTION

This invention relates to implantable medical devices, and more particularly to such devices with separate leads requiring attachment to the device.

BACKGROUND AND SUMMARY OF THE INVENTION

Implantable devices such as cardiac sensors, pacemakers, and defibrillators normally have a main housing implanted in a patient's pectoral or abdominal region. A flexible lead having one or more electrical conductors extends internally from the housing to the patient's heart. In a typical application, the lead is inserted endocardially, extending from the housing through an incision in a major vein, through the vein, and into the chamber of the heart. A sensor on the distal end of the lead may contact the cardiac tissue for sensing and stimulating the tissue.

The surgical process of inserting and positioning the lead requires skill and precision, and is typically performed by inserting the lead alone without the housing attached. Guiding the lead through the venous system may also require the insertion of stylets in a hollow lumen of the lead, as accessed from the proximal end. Therefore, detachable and reattachable leads are normally used, with the leads being connected to the housing after proper insertion and placement. The connection process occurs during surgery, after lead insertion and before housing implantation. Therefore, it is desirable that the connection process be achieved quickly, and with a high degree of confidence that a proper connection has been made.

In existing apparatus, the lead has an elongated male proximal end lead connector that is received by an elongated bore defined in a header portion of the housing, with the electrical and mechanical connection being made deep within the bore of the header. Although the header portion may be somewhat transparent in the prior art, the small size of miniature connectors makes difficult the confirmation of proper insertion by viewing through the header material. The trend toward miniaturization of implantable devices only exacerbates this problem. Also, any new superior biocompatible materials with poor optical qualities would be unusable for such a header.

The surgeon may also rely on the apparent insertion depth or tactile feel to infer proper connection. However, this method has drawbacks since the lead connectors may give the illusion of being fully inserted when they are not, such as if a lead's sealing ribs are not adequately lubricated to slide readily into the bore, or if the lead becomes caught on a misaligned or misdimensioned part, or if a foreign particle interferes with the connection. An improper connection is normally discovered by testing the device before closing the patient's surgical wound. To test an implanted defibrillator, a test shock is given during sinus rhythm. To further test the device, fibrillation is then induced in the patient's heart, and the device is allowed to automatically detect the fibrillation and treat it with proper defibrillation therapy. If the device has a faulty lead connection and does not respond properly, a conventional defibrillator with external paddles is employed. External defibrillation carries risks that are preferably reduced by minimizing the number of bad connections. After a faulty connection is corrected, the test procedure is repeated. While somewhat reasonably effective, the existing connection techniques and apparatus have less than optimal certainty of connection, which can prolong the surgery and increase the risk to the patient. Also, a marginal connection may pass the initial test, but fail after implantation.

The preferred embodiment of the invention overcomes these limitations of the prior art by providing an implantable medical apparatus operable in conjunction with an attachable lead, and having a housing containing an electronic component, with a header connected to the housing and defining a cavity. A connector element is positioned within the cavity and is operably connected to the electronic component. A lens is connected to the header, such that the connector element may be viewed through the lens to facilitate confirmation of proper connection of a lead to the connector. The header may be transparent, and the lens or lenses either may be formed as part of the header, or may be detachable therefrom.

DETAILED DESCRIPTION OF A PREFERRED EMBODIMENT

Figure 1:
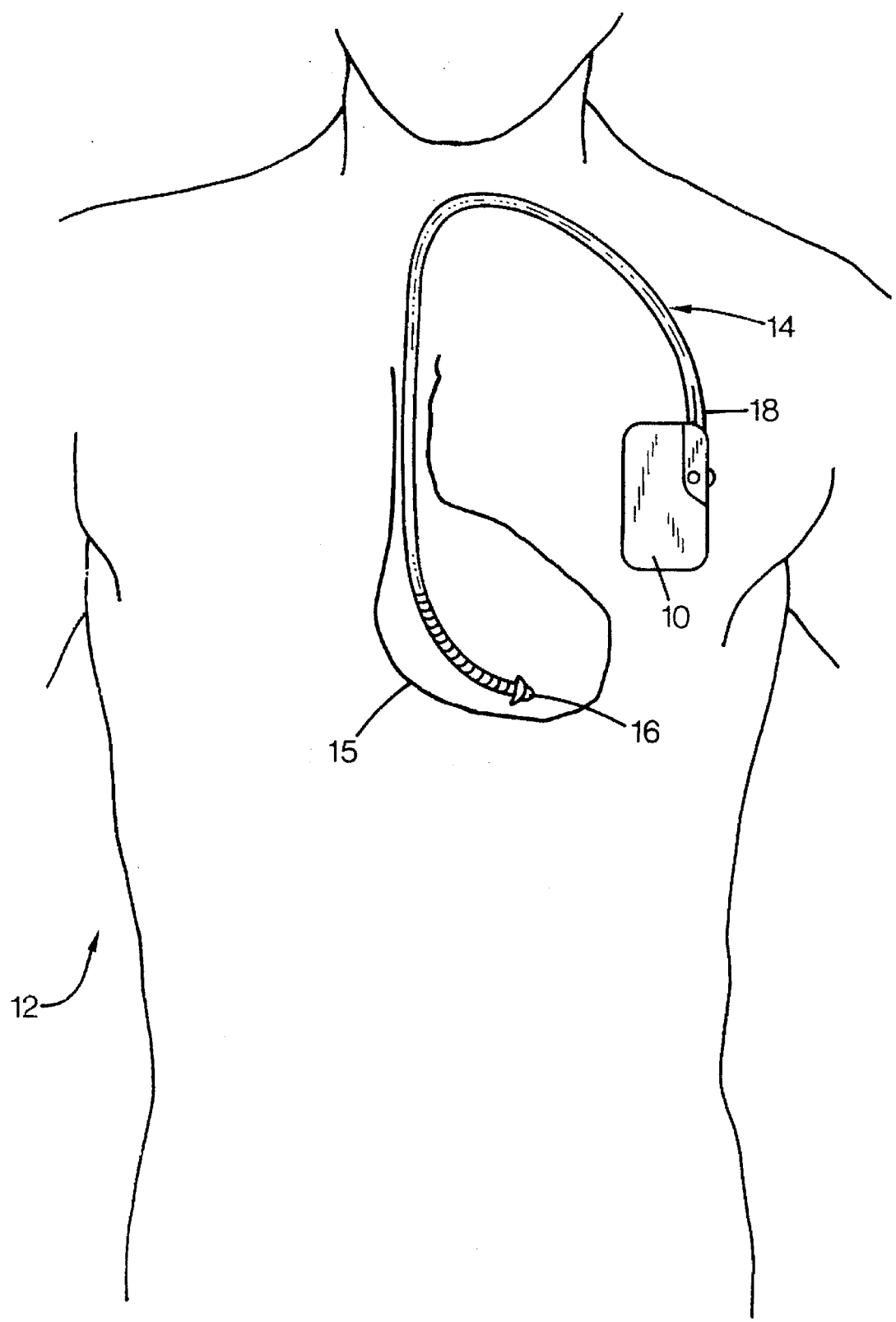
FIG. 1 is an overview of a preferred embodiment of the invention as implanted in a patient.

FIG. 1 illustrates an implantable defibrillator or pulse generator 10 according to the present invention as pectorally implanted in a patient 12. It may have bradycardia and antitachycardia pacing capabilities as well as cardioversion and defibrillation capabilities. A sensing and pacing lead connector 14 extends from the defibrillator 10 to the patient's heart 15. The lead has a distal end 16 within the heart, and a proximal end 18 having multiple end portions each containing a different conductor and separately attachable to the defibrillator. In the preferred embodiment, a four conductor lead is used.

Figure 2:
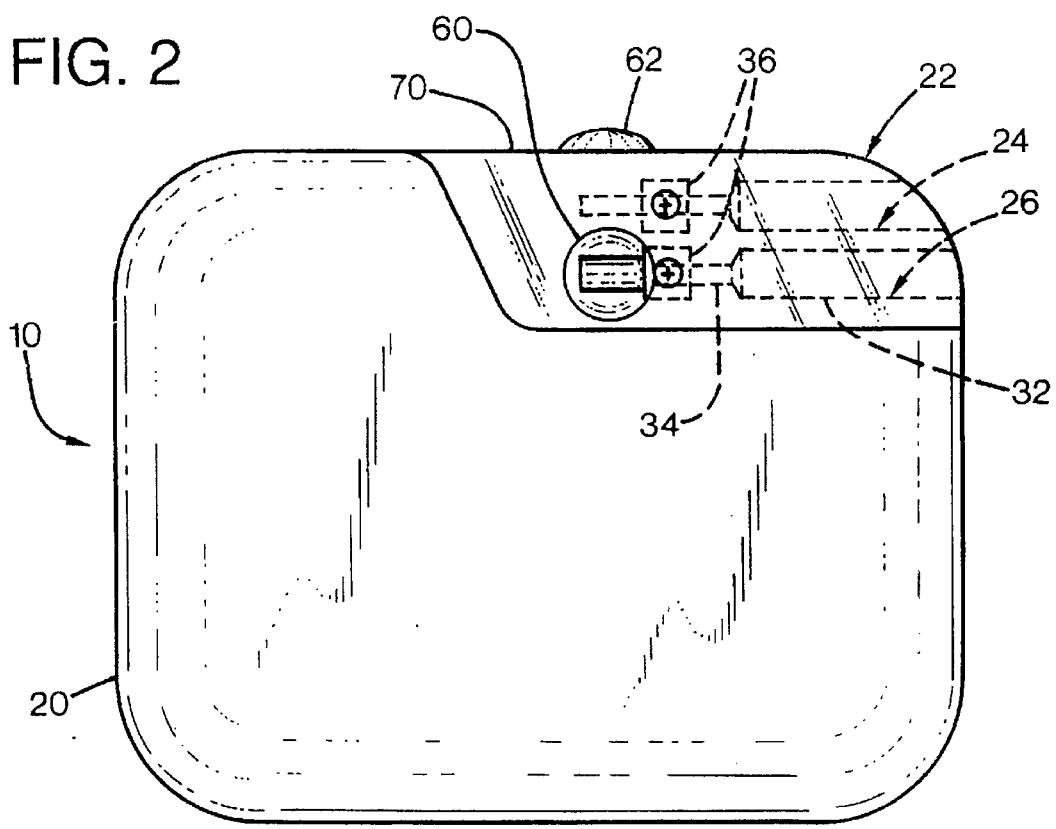
FIG. 2 is a front view of the embodiment of FIG. 1.
Figure 3:
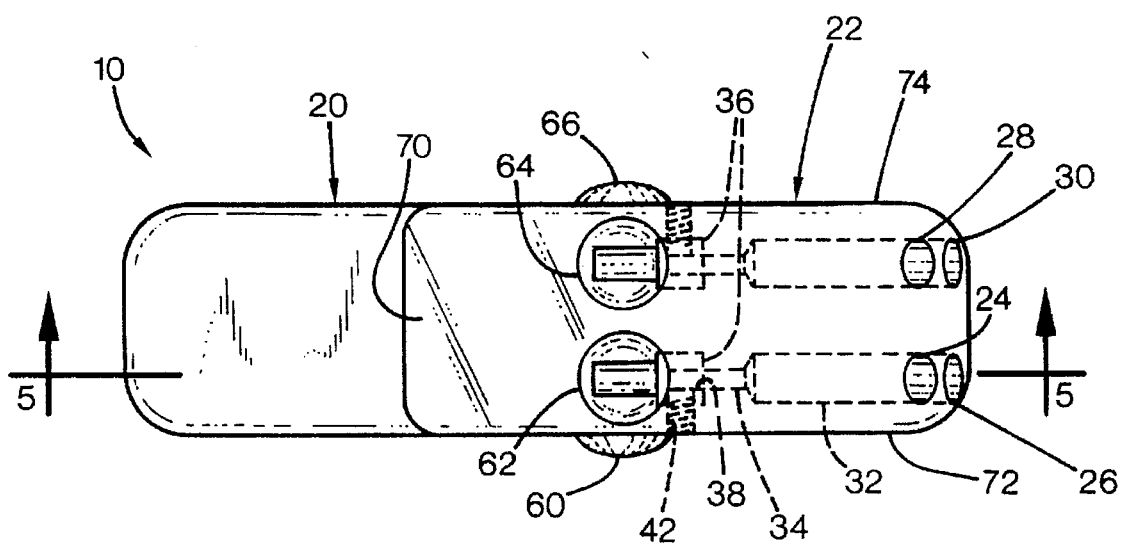
FIG. 3 is a top view of the embodiment of FIG. 1.

As shown in FIGS. 2 and 3, the defibrillator 10 includes a housing 20 formed of a corrosion resistant metal such as titanium, with numerous electronic components (not shown) contained within the housing. A header 22 is attached to or included as part of the housing 20, and is formed of a rigid transparent material such as epoxy, silicone rubber, or plastic. If not formed entirely of biocompatible material, the header may be formed of an optically clear material and coated by or encapsulated within a transparent or mildly translucent biocompatible material that is effectively transparent as a thin coating or shell.

Figure 4:
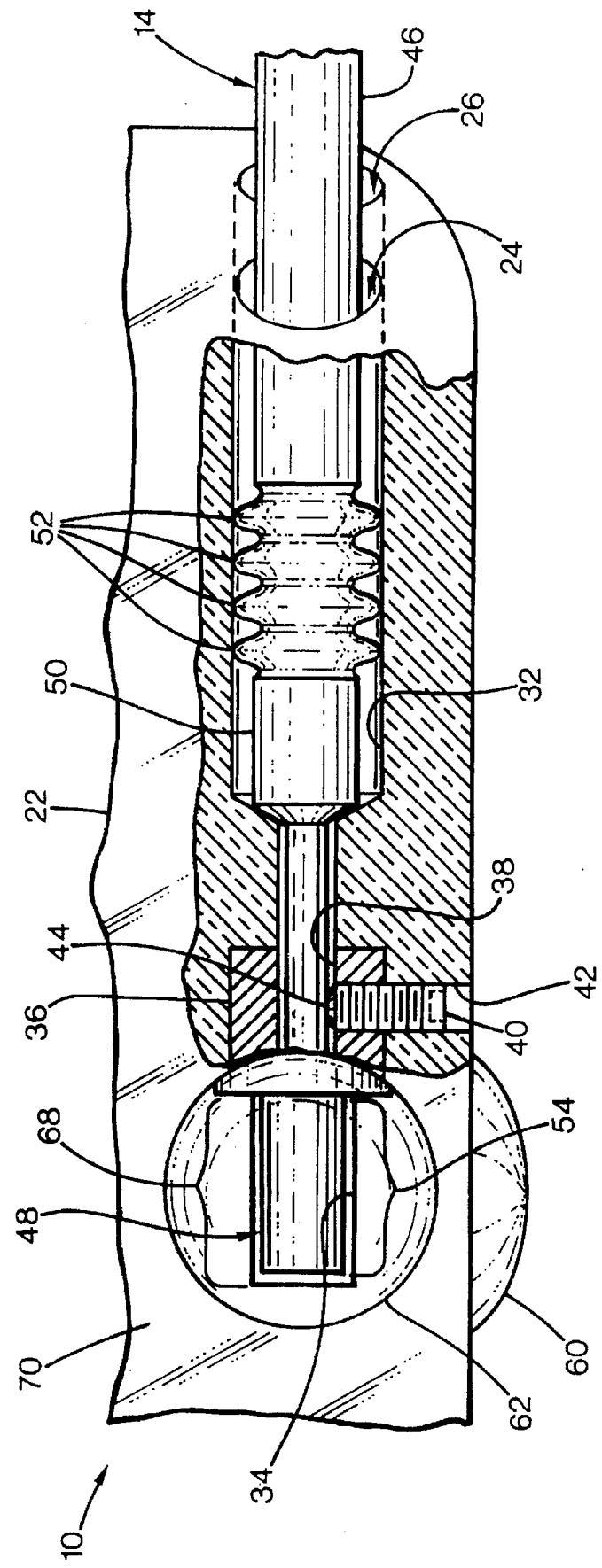
FIG. 4 is an enlarged top view of a portion of the embodiment of FIG. 1.

The header defines four lead connector cavities 24, 26, 28, and 30. Each cavity comprises an elongated cylindrical bore having a first diameter outer portion 32, and a smaller second diameter inner portion 34. As best shown in FIG. 4, a metal connector element or block 36 is encapsulated within the header for each cavity, with a bore 38 through each connector block. Alternatively, the connector block may be positioned within the header without encapsulation. The bore 38 is smoothly registered with the inner portion of the cavity such that the bore's conductive surface is exposed within the cavity. Each connector block 36 includes a set screw 40 on an axis perpendicular to the axis of the bore. The set screw 40 passes through a threaded bore 42 in the header and is threadably received by the connector block 36 so that the nose 44 of the set screw may enter the bore. The set screw may be turned to advance into the bore to provide mechanical clamping and electrical contact to a metallic element that may be inserted into the bore, as discussed below. Alternative connection mechanisms may employ leaf springs, garter springs, or other conventional electrical connectors instead of the preferred set screw mechanism.

As shown in FIG. 4, the lead connector 14 is installed fully in the header. In the preferred embodiment, The lead includes four proximal branches 46, with each branch inserted in a respective header cavity. Each lead branch includes a terminal connector pin 48 at its free end, and an insulated portion 50 adjacent the pin. The insulated portion has several resilient circumferential sealing ridges 52 that are slightly larger than the diameter of the first portion 32 of the bore to provide a seal. The connector pin 48 is a rigid cylindrical metal element having a diameter and length slightly smaller than the diameter and depth of the inner portion 34 of the cavity. As fully inserted, the connector pin 48 includes a protruding tip portion 54 that extends beyond the connector block 36. This ensures that the entire length of the bore 38 is fully occupied by the connector pin to provide a good mechanical and electrical connection.

Returning to FIGS. 2 and 3, the header includes four integrally formed lenses 60, 62, 64, and 66, each positioned over a respective cavity to provide a magnified image of the deepest portion 68 of the cavity, which extends beyond the connector block 36 to the end of the cavity. With the two-by-two cavity arrangement shown, the upper cavities 24 and 28 are viewed through side-by-side lenses 62 and 64 on the upper surface 70 of the header. Cavity 26 is viewed through lens 60 on the front side 72 of the header; cavity 30 is viewed through lens 66 on the rear side 74 of the header.

Figure 5:
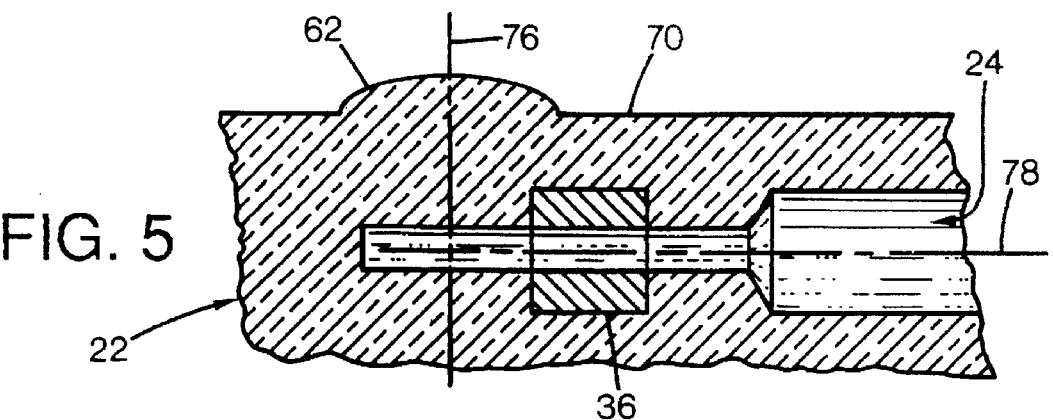
FIG. 5 is an enlarged sectional side view of the embodiment of FIG. 1.

Each lens has a positive curvature to provide a magnified image. The diameter of each lens should permit viewing a substantial portion of the deepest portion 68 of the cavity to determine whether the tip 54 is properly installed. Preferably, the view should show the edge of the connector block and the end of the cavity. For a 2 X magnification, the lens should have a diameter about double the distance between the connector block 36 and the base of the cavity. In the preferred embodiment, the lens may have a magnification in the range of slightly greater than one to ten times, with two to three times being preferred. As shown in FIG. 5, the lens 62 is a spherical surface oriented on an optical axis 76 perpendicular to the surface 70 on which the lens is formed. The optical axis is perpendicular to and intersects a cavity axis 78, providing a centered image. To provide an upright image, the lens surface may be spaced apart from the cavity axis by a distance less than the focal length of the lens, which is about double the lens's radius of curvature.

Figure 6:
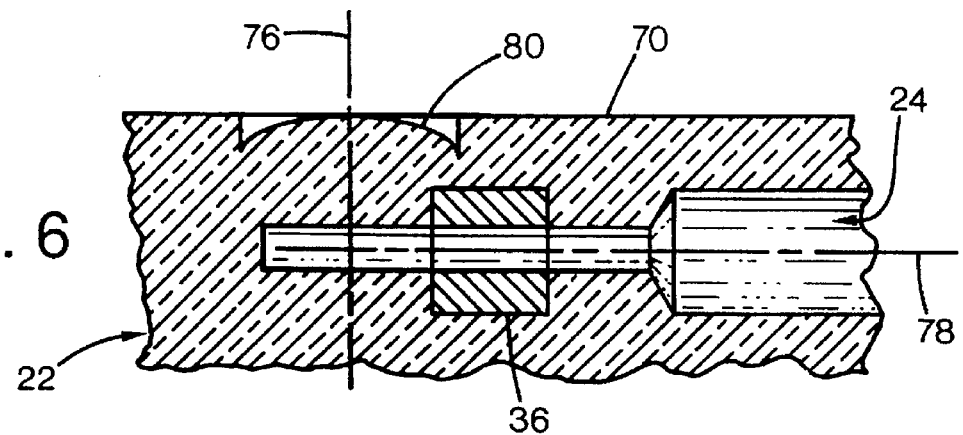
FIG. 6 is an enlarged sectional side view of a first alternative embodiment of the invention.
Figure 7:
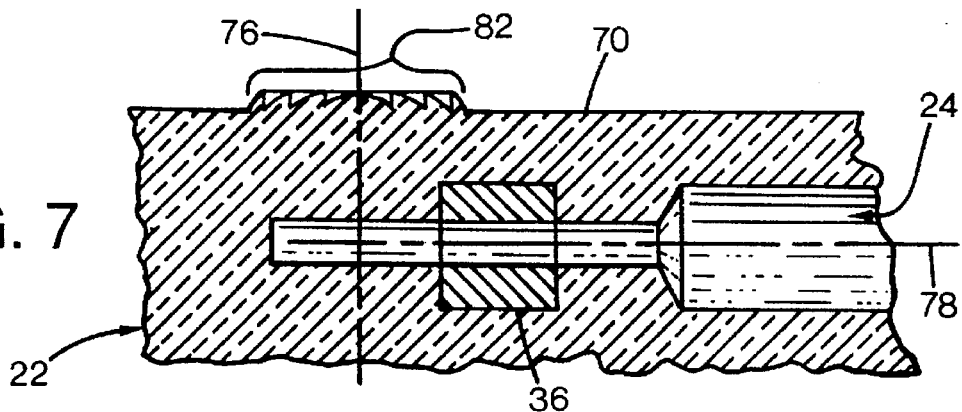
FIG. 7 is an enlarged sectional side view of a second alternative embodiment of the invention.
Figure 8:
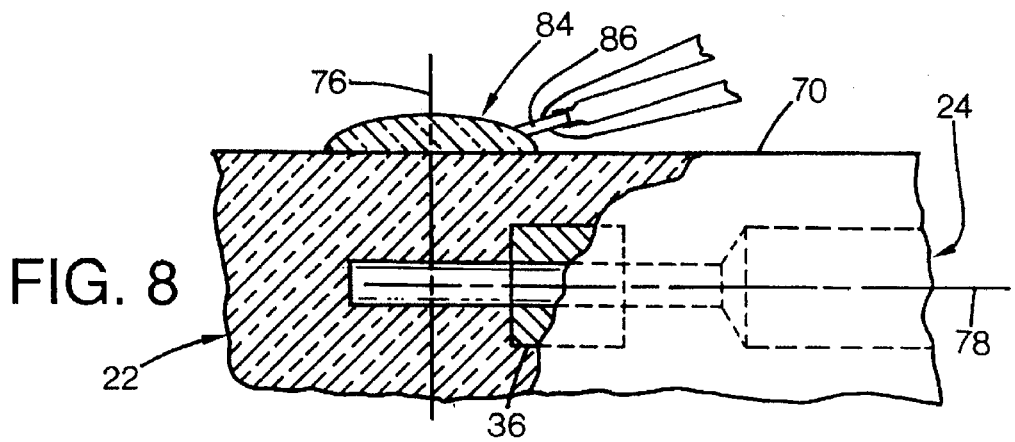
FIG. 8 is an enlarged sectional side view of a third alternative embodiment of the invention.

FIGS. 6, 7, and 8 show alternative lens configurations that achieve the same effect as the preferred embodiment. FIG. 6 shows a recessed lens 80 for applications in which abrasion of a protruding lens may be a concern. Where there is adequate volume in the header, this recessed embodiment provides reduced weight and volume. FIG. 7 shows a fresnel lens 82 to provide a lower profile for reduced volume and weight without forming pockets intruding into the header volume below the surface 70. The fresnel lens is appropriate where moisture and/or contamination are not likely to wet or obscure the prismatic ridges of the lens.

Figure 11:
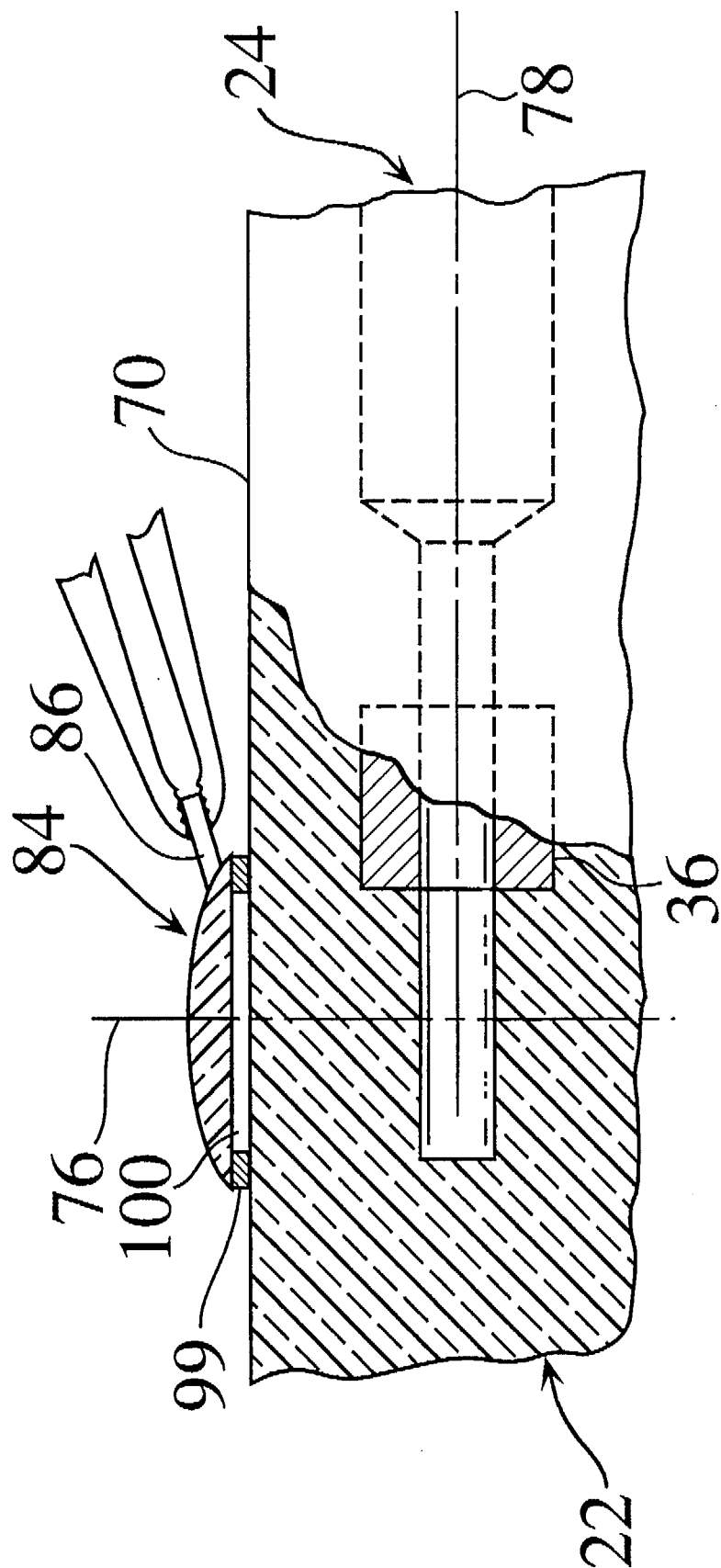
FIG. 11 is an enlarged sectional side view of a sixth alternative embodiment of the invention.

FIG. 8 shows a removable lens 84 that is connected to the header before and during connection of the leads, and which may be removed prior to implantation of the device. The lens 84 may be a transparent elastomer having a smooth lower surface that "wets" to the header surface 70 to provide the effect of an immersion lens, i.e. with no air gap to degrade image quality or collect moisture or contaminants. A rigid removable lens with an adherent lower surface may also be used, as may a rigid lens with releasable adhesive 99 at its periphery which separates lens 84 from header surface 70 by an air gap 100 as shown in FIG. 11. A raised or non adhered tab 86 at the edge of the lens permits it to be readily removed with forceps as shown.

Figure 9:
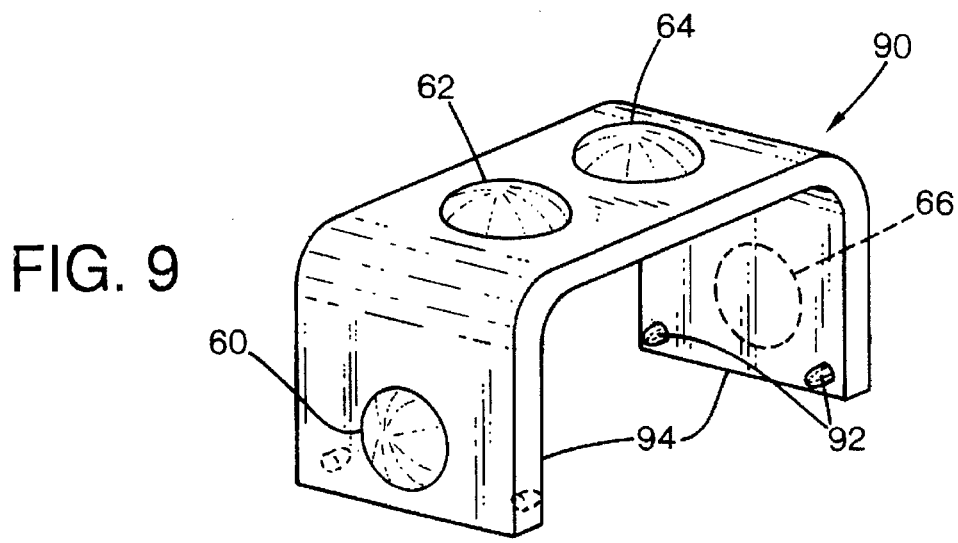
FIG. 9 is an enlarged sectional side view of a fourth alternative embodiment of the invention.

FIG. 9 shows a lens attachment 90 formed of a rigid transparent material for removably attaching to a header that lacks magnification lenses. The lens attachment is saddle shaped as an inverted U-shaped channel, and includes small bosses 92 at the lower edges of the inwardly facing surfaces of the downwardly depending side walls 94. The bosses 92 may engage corresponding dimples (not shown) formed in the header of a device, such that the lens attachment may be snapped onto the header as needed for inspection of the connection, and removed for implantation of a lensless device.

Figure 10:
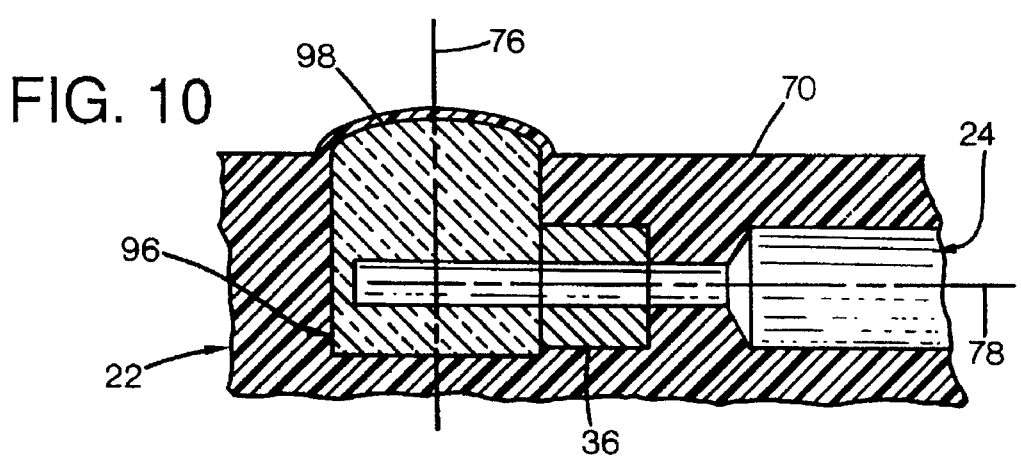
FIG. 10 is an enlarged sectional side view of a fifth alternative embodiment of the invention.

An alternative embodiment may require that the header be formed of a biocompatible material that is not optically clear, but is translucent, yellow, hazy, or contains distorting flow lines. In this case, the header may have an inner body formed of a material selected for its optical qualities, and coated on all external surfaces with the biocompatible material. The coating should be sufficiently thin that the degrading effects of the biocompatible material are minimal. Alternatively, as shown in FIG. 10, the header may be formed mostly of the biocompatible material, with only an optical tunnel 96 of clear material defining the inner end of the cavity and extending nearly to the lens surface, where it is coated by the biocompatible material 98. Such a header may be formed by insert molding the connector block 36 to the clear tunnel element 96, then insert molding or casting the block and tunnel within the header.

While the disclosure is described in terms of a preferred embodiment, the following claims are not intended to be so limited.

I claim:

1. An implantable medical apparatus operable in conjunction with attachable lead, the apparatus comprising:

a housing;

an electronic component contained within the housing;

a header connected to the housing, the header defining a connector cavity, wherein at least a portion of the header is transparent or translucent;

a connector element, at least a portion of which is positioned within the connector cavity, the connector element being operably connected to the electronic component; and the header including a flexible lens, such that the connector element may be viewed through the lens to facilitate confirmation of proper connection of a lead to the connector element, wherein the lens is removable from the header, such that the lens may be removed after confirming that the lead is properly connected.

2. An implantable medical apparatus operable in conjunction with an attachable lead, the apparatus comprising:

a housing;

an electronic component contained within the housing;

a transparent header connected to the housing, the header defining a connector cavity;

a connector element, at least a portion of which is positioned within the connector cavity, the connector element being operably connected to the electronic component; and the header including a lens, such that the connector element may be viewed through the lens to facilitate confirmation of proper connection of a lead to the connector element, wherein the lens is separated from the header by an air gap.

3. An implantable medical apparatus operable in conjunction with an attachable lead, the apparatus comprising:

a housing;

an electronic component contained within the housing;

a header connected to the housing, the header defining a connector cavity, wherein at least a portion of the header is transparent or translucent;

a connector element, at least a portion of which is positioned within the connector cavity, the connector element being operably connected to the electronic component; and the header including a lens, such that the connector element may be viewed through the lens to facilitate confirmation of proper connection of a lead to the connector element, wherein the lens is removable from the header, such that the lens may be removed after confirming that the lead is properly connected wherein the lens is made of an elastomer.

4. An implantable medical apparatus operable in conjunction with an attachable lead, the apparatus comprising:

a housing;

an electronic component contained within the housing;

a header connected to the housing, the header defining a connector cavity, wherein at least a portion of the header is transparent or translucent;

a connector element, at least a portion of which is positioned within the connector cavity, the connector element being operably connected to the electronic component; and the header including a lens, such that the connector element may be viewed through the lens to facilitate confirmation of proper connection of a lead to the connector element, wherein the lens is removable from the header, such that the lens may be removed after confirming that the lead is properly connected, wherein the lens has a smooth lower surface that wets to the header surface to provide the effect of an immersion lens.

5. An implantable medical apparatus operable in conjunction with an attachable lead, the apparatus comprising:

a housing;

an electronic component contained within the housing;

a header connected to the housing, the header defining a connector cavity, wherein at least a portion of the header is transparent or translucent;

a connector element, at least a portion of which is positioned within the connector cavity, the connector element being operably connected to the electronic component; and the header including a lens, such that the connector element may be viewed through the lens to facilitate confirmation of proper connection of a lead to the connector element, wherein the lens is removable from the header, such that the lens may be removed after confirming that the lead is properly connected, wherein the lens is formed on a saddle-shaped attachment that forms a U-shaped channel.

6. The apparatus of claim 5 wherein the saddle-shaped attachment includes small bosses on the inwardly facing surfaces of the U-shaped channel, and wherein the header includes corresponding dimples formed therein, such that the attachment may be snapped onto the header.

7. An implantable medical apparatus operable in conjunction with an attachable lead, the apparatus comprising:

a housing;

an electronic component contained within the housing;

a header connected to the housing, the header defining a connector cavity, wherein at least a portion of the header is transparent or translucent;

a connector element, at least a portion of which is positioned within the connector cavity, the connector element being operably connected to the electronic component; and the header including a lens, such that the connector element may be viewed through the lens to facilitate confirmation of proper connection of a lead to the connector element, wherein the lens is removable from the header, such that the lens may be removed after confirming that the lead is properly connected, wherein the lens includes a raised tab to facilitate removal.

8. A method of implanting a medical device in a patient comprising the steps of:

providing a device having a header having a lens portion and defining a cavity in which a connector may reside;

inserting a distal end of an elongated lead into the patient;

inserting a proximal end of the lead into the connector;

viewing the proximal end through the lens portion of the header;

confirming correct insertion of the proximal end;

removing the lens from the device; and implanting the device into the patient without the lens.

9. The method of claim 8 including transmitting light through the header to illuminate the connector.

10. The method of claim 8 and further including the step of attaching the lens to the header, prior to said step of viewing the proximal end through the lens portion of the header.

11. The method of claim 10 wherein the step of attaching the lens to the header includes wetting the lens to the header surface to provide the effect of an immersion lens.

12. The method of claim 10 wherein the lens is formed on a saddle-shaped attachment that forms a U-shaped channel, and wherein the step of attaching the lens to the header includes snapping the attachment onto the header by engaging bosses in the attachment into dimples in the header.

13. The method of claim 8 wherein the lens has releasable adhesive at its periphery and wherein the step of removing the lens from the device includes the step of releasing the lens from the header surface.

14. The method of claim 8 wherein the step of removing the lens includes grasping a raised tab at the edge of the lens.

* * * * *